US012644863B2

(12) United States Patent
Lal et al.

(10) Patent No.: US 12,644,863 B2
(45) Date of Patent: Jun. 2, 2026

(54) IMAGING AND SENSING OF THIN LAYER USING HIGH-FREQUENCY ULTRASONIC TRANSDUCERS

(71) Applicant: GEEGAH LLC, Ithaca, NY (US)

(72) Inventors: Amit Lal, Ithaca, NY (US); Justin Kuo, Ithaca, NY (US)

(73) Assignee: GEEGAH LLC, Ithaca, NY (US)

( * ) Notice: Subject to any disclaimer, the term of this patent is extended or adjusted under 35 U.S.C. 154(b) by 295 days.

(21) Appl. No.: 18/266,101

(22) PCT Filed: Dec. 8, 2021

(86) PCT No.: PCT/US2021/062481
§ 371 (c)(1),
(2) Date: Jun. 8, 2023

(87) PCT Pub. No.: WO2022/125708
PCT Pub. Date: Jun. 16, 2022

(65) Prior Publication Data
US 2024/0036005 A1 Feb. 1, 2024

Related U.S. Application Data

(60) Provisional application No. 63/122,520, filed on Dec. 8, 2020.

(51) Int. Cl.
*G01N 29/036* (2006.01)
*A61B 8/00* (2006.01)
(Continued)

(52) U.S. Cl.
CPC ......... *G01N 29/036* (2013.01); *A61B 8/4483* (2013.01); *B06B 1/0622* (2013.01);
(Continued)

(58) Field of Classification Search
CPC .............. G01N 29/036; G01N 29/348; G01N 2291/0237; G01N 2291/0253;
(Continued)

(56) References Cited

U.S. PATENT DOCUMENTS

2004/0002655 A1    1/2004  Bolorforosh et al.
2013/0018266 A1    1/2013  Nishikubo et al.
(Continued)

FOREIGN PATENT DOCUMENTS

CN        109475299 A      3/2019
DE        102007047153 A1  4/2009
(Continued)

OTHER PUBLICATIONS

International Search Report and Written Opinion for PCT/US2021/062481, filed Dec. 8, 2021. Mailing Date of Search Report Mar. 29, 2022. pp. 1-12.
(Continued)

*Primary Examiner* — Benjamin R Schmitt
(74) *Attorney, Agent, or Firm* — George R. McGuire; Bond Schoeneck & King PLLC

(57) ABSTRACT

A system for measuring the environment using high-frequency ultrasonic pulses to interrogate thin films on the imaging surface of a CMOS integrated GHz Ultrasonic imager substrate. In one embodiment the device uses a Peltier cooler and heater chip to detect the dew point by the act of moisture condensing on the surface. Integrated temperature measurement is enabled by using some of the pixels, isolated from the environment, to be reflectors that measure the phase change in the reflected signal due to the change in the speed of sound in the silicon substrate. In another embodiment a thin film is exposed to gases, changing its ultrasonic impedance, which can be used to extract the film thickness and its ultrasonic properties.

17 Claims, 6 Drawing Sheets

(51) Int. Cl.
  *B06B 1/06*          (2006.01)
  *G01N 29/34*          (2006.01)
  *H10N 39/00*          (2023.01)
  *H10W 40/28*          (2026.01)

(52) U.S. Cl.
  CPC ........... *G01N 29/348* (2013.01); *H10N 39/00*
            (2023.02); *H10W 40/28* (2026.01); *G01N*
              *2291/0237* (2013.01); *G01N 2291/0253*
              (2013.01); *G01N 2291/02845* (2013.01)

(58) Field of Classification Search
  CPC ........ G01N 2291/02845; A61B 8/4483; B06B
              1/0622; H01L 23/38; H10N 39/00
  See application file for complete search history.

(56)                References Cited

U.S. PATENT DOCUMENTS

| | | | |
|---|---|---|---|
| 2013/0134528 | A1 | 5/2013 | Nguyen et al. |
| 2017/0098758 | A1 | 4/2017 | Iwamoto |

FOREIGN PATENT DOCUMENTS

| | | | | |
|---|---|---|---|---|
| KR | 20170099833 | A | 9/2017 | |
| WO | WO-2019152961 | A1 * | 8/2019 | ............. G01K 11/22 |

OTHER PUBLICATIONS

EP Partial Search Report, Application No. 21904354.4, dated Sep. 10, 2024, entire document.

* cited by examiner c.

b.

a.

IMAGING AND SENSING OF THIN LAYER USING HIGH-FREQUENCY ULTRASONIC TRANSDUCERS

CROSS-REFERENCE TO RELATED APPLICATION

This application is a U.S. National Stage application based on International Application PCT/US21/62481, filed Dec. 8, 2021, which claims priority to U.S. Provisional Patent Application Ser. No. 63/122,520, filed on Dec. 8, 2020 and entitled "Imaging and Sensing of Thin Layer Using High-Frequency Ultrasonic Transducers," the entire disclosure of each of which is incorporated herein by reference.

GOVERNMENT FUNDING

This invention was made with Government support under Grant Number AR0001049 awarded by the Department of Energy. The United States Government has certain rights in the invention.

FIELD OF THE INVENTION

The present disclosure is directed generally to technology for transmitting GHz ultrasonic pulses through a substrate by using thin piezoelectric transducers formed on the substrate.

BACKGROUND

There are many needs for sensors that can image and sense environmental variables. Dew point is an important variable that needs to be measured to determine the condensation properties of gases. Condensing of water on surfaces or condensation of other gases onto surfaces can lead to corrosion. In the field of chemical engineering, a network of pipes is used to carry gases from storage cylinders to reaction chambers. During the gas transport to a reaction chamber or from a chamber, the purity of the gases needs to be highly regulated. For example, when methane is produced, its water content is to be reduced for the gas to be used in its purest formulation. Hence, water moisture sensors in gases are often used to track the amount of water in vapors. In another application, humidity is measured regularly in food storage areas where excess moisture can affect food quality with regards to aging and potential growth of bacterial and fungal films. Another application of humidity and dew point sensing is tamper measurement/detection. For example, expensive and valuable materials, such as medicine can be packaged in air-tight containers in an environment consisting of inert gases such as nitrogen, or even under vacuum. This is sometimes done to detect tampering to the package. An act of tampering, for example in order to extract the medicine, leads to a break in the package and exposure to air. A tamper event is important to detect to be able to follow the transport of said medicine through the supply chain. In some applications, it is important to determine if a sample was exposed to air if packaged in a dry gas such as nitrogen. For example, drugs can be sealed in a non-air environment such as nitrogen to extend the drug's life against oxidation with air.

In order to measure the dew point, several sensor technologies have been developed. These include the use of laser beams to reflect off chilled mirrors, the reflectance of which can vary owing to formation of ice or water. A separate temperature sensor is needed to monitor the cooling by an active cooler in all these approaches. Capacitive sensors are also used to measure the change in capacitance owing to water condensation, which has a high dielectric constant compared to air. The capacitance can also change in capacitive sensors due to surface contaminants and is generally not as accurate as that of the chilled mirror approach. The capacitance measurement approach leads to signal drift over time. Another approach is to place polymer coating as capacitors that absorb moisture and provide a signal's capacitance change. A third technology used for dew point sensing is quartz crystal microbalances to measure absorbed water on the surface of a resonant quartz crystal. As water adsorbs, the added mass is measured due to the shift in the resonance frequency of operation. This device can suffer due to drift of the resonance frequency, and the sensitivity can suffer due to the small fractional change in the mass compared to the bulk mass of the crystal. Further quartz crystal devices are typically bulky and require separate devices connected to the electronic circuits to drive the crystals. Quartz crystal devices typically operate at MHz frequencies, with milli-meter scale wavelengths in liquids and solids. A resonant thin film on the surface would be very thick and hard to fabricate accurately.

Generally, the optical reflectance method leads to the highest sensitivity and repeatability sensor. Optical wavelengths are in the sub-micron regime, where the light interacts with a thin layer providing for interactions with a film thinner than the wavelength. However, because optical approach requires an optical source and optical components, the assembly is typically large and cannot be miniaturized, and generally requires the assembly of multiple components. Recent methods have demonstrated the use of integrated photonics optical waveguides to replace free-space optics, in an attempt to reduce the volume and assembly required. Even with this approach, a separate assembly of the LED or laser light source is needed.

Accordingly, there is a need in the art for a small truly single chip, monolithically integrated dew point that can be produced at a low cost.

SUMMARY

Complementary metal-oxide-semiconductor (CMOS) technology enables hundreds to thousands of devices to be made on each wafer, enabling repeatability and low cost. Such a small device can be placed inside small bottles, or inside pipes and be read out remotely through wireless or ultrasonic communications links, potentially providing energy to the sensor. A sensor that can accomplish high accuracy and repeatability can be accomplished by integrating directly into a CMOS substrate, to provide both digital and analog circuitry to feedback control on the sensor within the same chip would enable the tracking of sensor performance over time, and have enough local computation capability to provide events that can lead to sensor failure.

A sensor can be formed by applying a thin layer of hygroscopic material such as calcium carbonate on an (Ultrasonic) US sensor. As the moisture goes in and out of the film, the films US impedance will change, allowing one to measure the thin film's exposure to moisture. The sensor chip can be placed inside bottles and interrogated using Radio Frequency (RF) pulses through an integrated antenna or have the sensor interfaced to a Radio Frequency Identification (RFID). To sense oxygen, the thin layer can be a layer of material that oxidizes quickly, such as iron. Iron will turn in iron-oxide, and its ultrasonic impedance will change over time and be measured using the ultrasonic pulses sensor.

The present disclosure is directed to the use of high frequency ultrasonic pulses, with carrier frequencies greater than 900 MHz, that can be used to interrogate thin films on the back side of a substrate. The thin film interrogation allows the measurement of the dew point by measuring thin films of water condensing due to decreased temperature, moisture in air through absorption in hygroscopic thin films, and oxygen through reaction with a thin iron layer. The miniature nature of the chip due to high degree of integration enables extremely tiny sensors and imagers that can be placed in small cavities and packages. The low power nature of the devices also enables the options for battery power or RF power.

In one embodiment the frequencies are in the gigahertz range where the wavelengths are in the range of a few micrometers thus enabling very thin films to be used as added elements.

According to an aspect a sensor comprising a substrate with integrated electronics having a first and a second side; a piezoelectric transducers connected to the first side of the substrate; and a thin solid layer connected to the second side of the substrate.

According to an embodiment, the piezoelectric transducer operates at frequencies at least 900 MHz.

According to an embodiment, there are a plurality of piezoelectric transducers that are formed in an array.

According to an embodiment, the substrate comprises integrated CMOS electronics.

According to an embodiment, further comprising a RF receiver and transmitter, including integrated antennas to enable remote measurement.

According to an embodiment, the piezoelectric transducer pixels sensors are arranged in a 2D array producing images of the changes in the thin film.

According to an embodiment, the thin layer is a moisture absorbing layer that is configured to absorb moisture in the air.

According to an embodiment, the thin layer is calcium carbonate.

According to an embodiment, the thin layer is an evaporated metal layer that can chemically react with the environment.

According to an embodiment, the thin layer is iron.

According to an embodiment, the thickness of the thin layer is no greater than 5 micrometers.

According to an aspect a sensor comprising a substrate with integrated electronics having a first and a second side; a piezoelectric transducers connected to the first side of the substrate; and a cooling element connected to the second side of the substrate.

According to an embodiment, the piezoelectric transducer operates at frequencies at least 900 MHz.

According to an embodiment, there are a plurality of piezoelectric transducers that are formed in an array.

According to an embodiment, the substrate comprises integrated CMOS electronics.

According to an embodiment, further comprising a RF receiver and transmitter, including integrated antennas to enable remote measurement.

According to an embodiment, the piezoelectric transducer pixels sensors are arranged in a 2D array producing images of the changes in the thin film.

According to an embodiment, the thin layer is a moisture absorbing layer that is configured to absorb moisture in the air.

According to an embodiment, the thin layer is calcium carbonate.

According to an embodiment, the thin layer is an evaporated metal layer that can chemically react with the environment.

According to an embodiment, the thin layer is iron.

According to an embodiment, the thickness of the thin layer is no greater than 5 micrometers.

According to an aspect a sensor the process of imaging and sensing the environmental gases and the dew point consisting of the steps comprise placing the imager in an environment and scanning through an ultrasonic transducer; recording a return signal as a function of an ultrasonic carrier frequency; recording a temperature of an imager chip using a phase shift of an ultrasonic pulse reflection; recording a temperature using electronic temperature sensors; and controlling an imager substrate temperature using the a cooling and heating element.

These and other aspects of the invention will be apparent from the embodiments described below.

BRIEF DESCRIPTION OF THE DRAWINGS

The present invention will be more fully understood and appreciated by reading the following Detailed Description in conjunction with the accompanying drawings, in which.

DETAILED DESCRIPTION OF EMBODIMENTS

Figure 1:
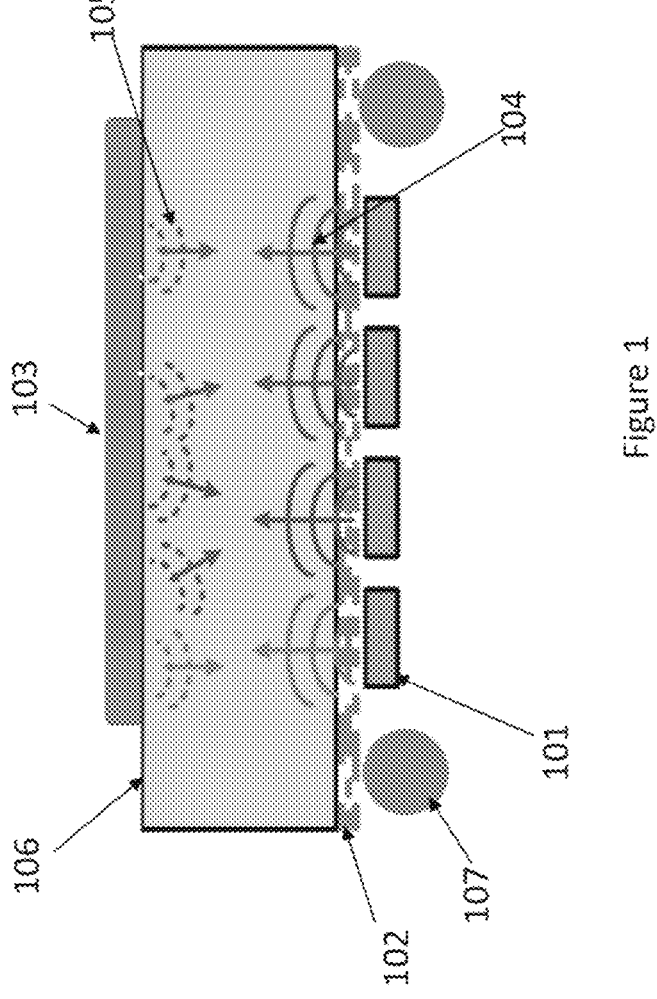
FIG. 1 is a schematic view of a sensor, in accordance with an embodiment.

The present disclosure describes a chip-based sensing technology that utilizes piezoelectric thin films on CMOS substrates (FIG. 1). According to one embodiment, the piezoelectric thin films transducers 101 are actuated electrically using CMOS circuits 102 right below the transducers, in the thickness mode resonance frequency of the transducers, typically in the GHz frequency range. Wire bonds or flip-chip bonding metal or solder balls/bumps 107 attach the imager chip to a PC board for connection to supporting analog and digital electronics. The CMOS circuits monolithically attached to the transducers minimizes the parasitic capacitances and offers highest performance. However, CMOS electronics can be integrated with the transducer array by bonding of a transducer array chip to a CMOS chip. This latter approach can allow a greater number of choices for the substrate carrying the ultrasonic pulses. An ultrasonic pulse packet 104, consisting of several number of cycles is transmitted through the substrate, most typically silicon in the case of CMOS implementation. The pulse packet travels to the opposite side of the wafer and reflects back as a packet 105. This transduction of a transmitted and received pulse has been used to image fingerprints, soil, and nematodes in soil, etc. on the opposite of the CMOS side, also called the imaging side 106. The pulses are short enough, spanning 50-100 microns, such that the reflected pulses from the opposite side of the substrate 106 are distinguishable in time from the transmitted pulses. This reflected pulse is modified by the effective ultrasonic impedance looking into the reflecting interface between the substrate and air or potentially condensed liquid layer. Furthermore, in one embodiment the substrate's temperature can be measured by the change in the time-of-flight or the change in the phase of the return signal due to the change in the speed of sound in the bulk materials. Hence with a few ultrasonic transducers, each a pixel transducer in an array of transducers, the temperature can be measured by a few pixels, and the thin solid or liquid layer 103 on the imaging surface can be measured and imaged using other pixels.

Figure 2:
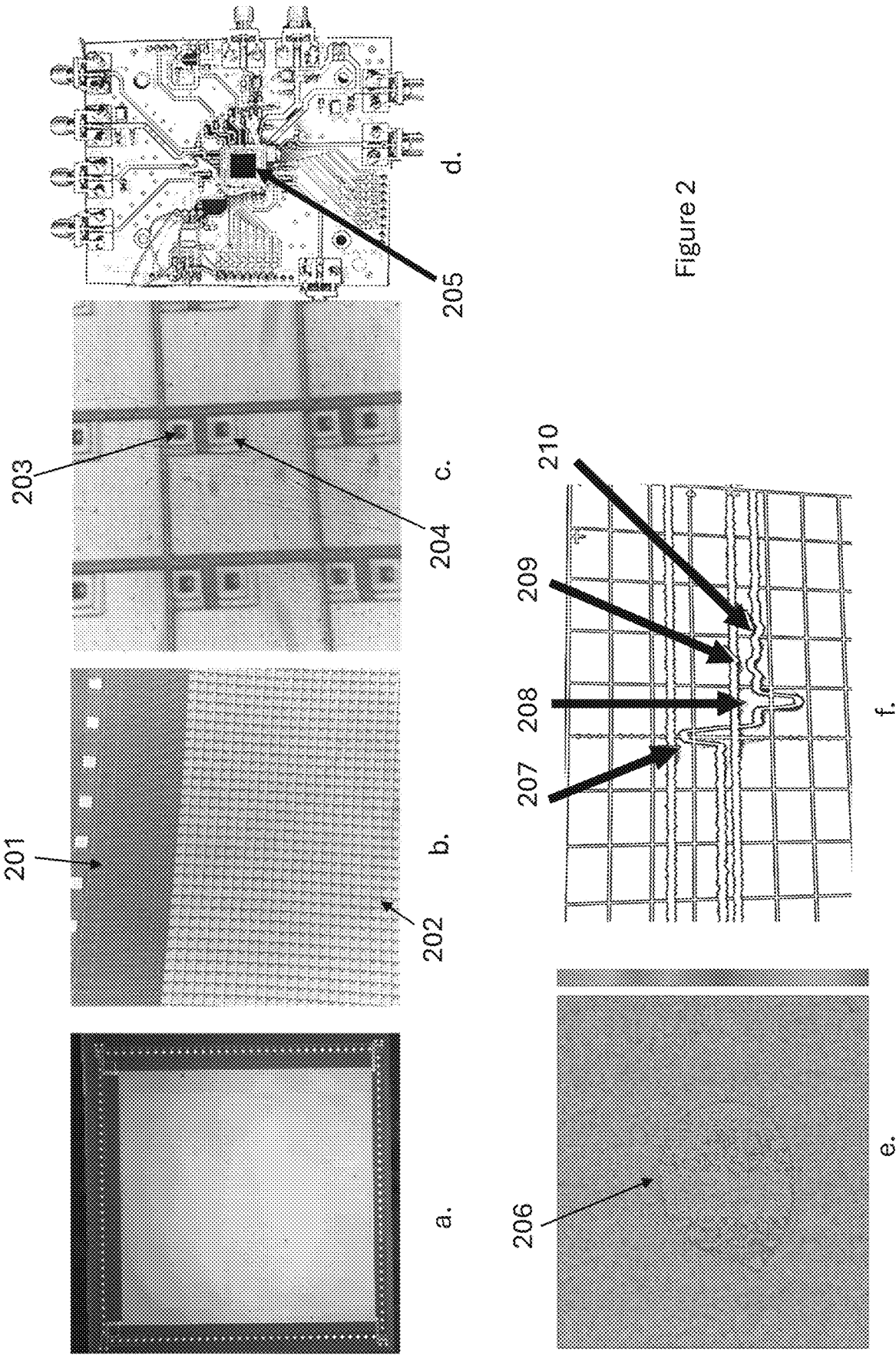
FIG. 2a is a US imager array of 128×128 pixels integrated in CMOS substrate.
FIG. 2b is a magnified view of the chip showing the bond pads and the pixel array.
FIG. 2c shows a magnified view of the pixels with the top and bottom connections and vias to the CMOS circuitry below the pixels.
FIG. 2d shows the chip mounted on a PCB that can consists of support circuitry to image each pixel.
FIG. 2e shows an ultrasonic image captured by the 128×128 pixel imager with a drop of water in the middle of the imager.
FIG. 2f shows the pulse sequence for each of the 128×128 pixel array. The first pulse received on the receiver electronics is the Rf coupling from the driver, followed by the first, second, and third echoes. The amplitudes of the reflected pulse amplitude can change as the received signal is generated through a RF mixer.

As shown in FIG. 2a, a 128×128 pixel array of aluminum nitride thin film transducers on 130 nm CMOS wafer has been fabricated to realize a real-time imager of objects placed on the back surface. FIG. 2b shows a closeup photograph of the chip showing the bond pads 201 and the array of pixels 202. FIG. 2c shows the 50×50 um pixel, with connections 203 and 204 to the top and bottom electrode of the piezoelectric film, which are then connected to CMOS circuitry below the pixels. FIG. 2d shows the chip bonded to a PC Board with ancillary electronics to scan through the pixels and measure the ultrasonic pulses. This board consists of analog circuitry to process the reflected signal to an ADC (Analog to Digital converter), VCO (Voltage Controlled Oscillator), and FPGA (Field Programmable Gate Array) to guide the timing of the signals and the row-column addressing needed to scan through the array. FIG. 2e shows an ultrasonic image obtained of a drop of water resting on the imager surface. Note that the bands in the middles of the water droplet are due to crossover sensitivity variation across columns of 32 pixels. This variation can be cancelled out by calibration in air. The shape and size of the droplet changes as the water evaporates. The droplet evaporation and addition are captured in real time movie formats at 10-15 frames per second. For each pixel we receive an analog signal as shown in FIG. 2f. The return ultrasonic pulse is converted into an electrical RF pulse through the piezoelectric effect. The signal is than mixed with the VCO that generated the transmitted pulse. The mixed signal results in a baseband envelope of the pulses as seen on the oscilloscope trace in FIG. 2f. The first pulse 207 is the pulse obtained when the transmitted signal couple into the receiver. The first reflected signal echo 208, and second and third echoes (209 and 210 respectively) are also shown. The amplitude can change since the receiver mixes the incoming signal with the VCO and therefore is sensitive to the phase of the incoming pulse. Both the I and Q part of the return pulse can be obtained by mixing the VCO frequency and its 90-degree phase shifted version with the return signal. The values of I and Q allows the calculation of the total phase of the return pulse with respect to the transmitted pulse.

When a thin liquid or solid film 103 (FIG. 1) is present on the device surface, the waves can propagate through the layer, and be reflected from the layer-air interface, and add to the pulse being reflected from the silicon-layer interface. The pulse packet can also bounce back from the substrate-layer interface and add constructively or destructively creating a thin film resonator structure on top of the substrate. This results in a thickness-dependent reflection coefficient for the pulse-packet as see at the silicon-layer interface. This impedance can be derived to be $Z_{in}=Z_{layer}\,\mathrm{Tan}(\beta l_{layer})$ where $Z_{layer}$ is the ultrasonic impedance of the layer material which is typically written as $Z=\rho v$ where $\rho$ is the density, and $v$ is the speed of sound in the material. The quantity $\beta$ is the propagation wavenumber lay $$\left(\beta = \frac{2\pi}{\lambda} = \frac{2\pi f}{v}\right),$$

which can be a complex number with real and imaginary components, where the imaginary component corresponds to the loss in the material. The input impedance can be used to calculate the reflection coefficient at the substrate-layer interface as $$R = \frac{Z_{in} - Z_{sub}}{Z_{in} + Z_{sub}}.$$

This reflection coefficient can be a complex number due to the imaginary component of the propagation coefficient $\beta$. The magnitude of the reflection coefficient can be plotted as a function of the thin layer thickness. As the water layer thickness is increased the wave coupled into the layer thickness decays such that a very small amount of energy is available to bounce back and forth within the layer.

Figure 3:
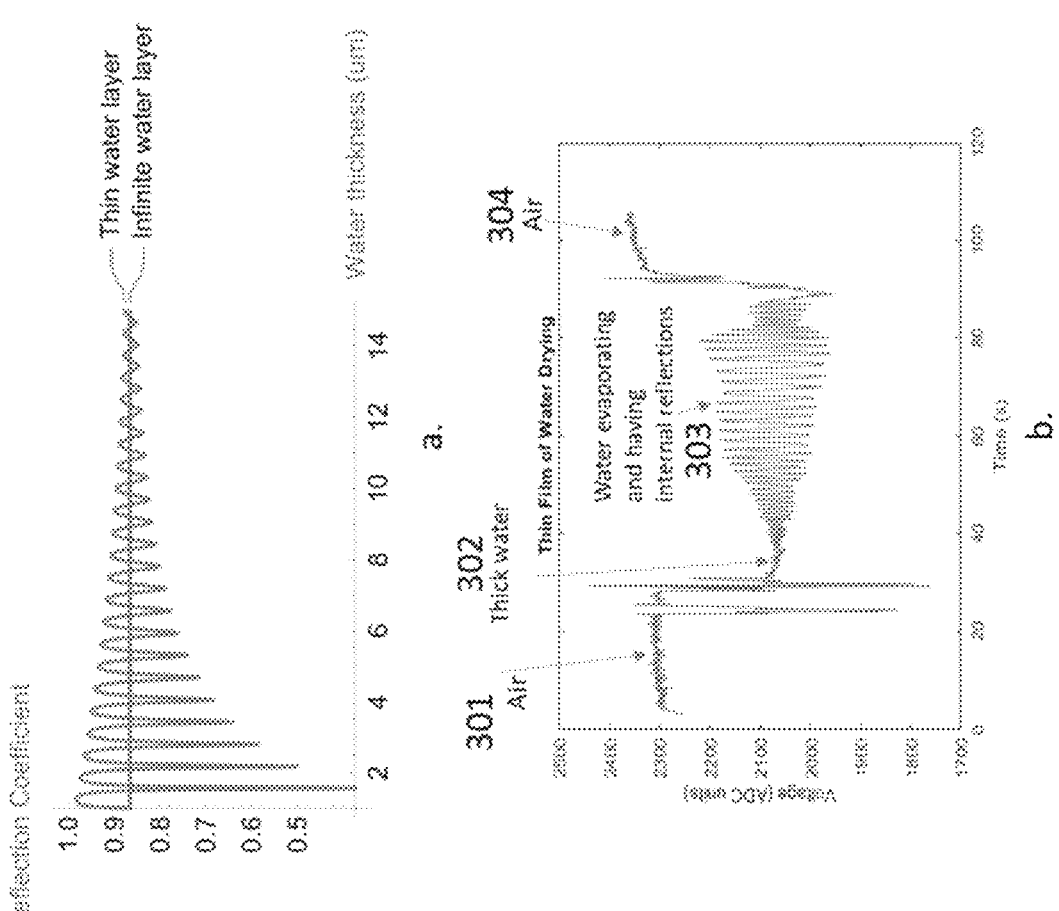
FIG. 3a graph of a simulation of the reflectance coefficient for the US pulses as a function of water layer thickness at GHz frequencies, in accordance with an embodiment.
FIG. 3b is a graph of the measured reflected signal from a layer of water deposited on the backside indicated resonances in the thin film as the water layer gets thinner, in accordance with an embodiment.

FIG. 3a plots the calculated the reflection coefficient for a thin water layer on the substrate, as a function of the thin water layer. The plot shows maximum and minima in the reflection coefficient due to the resonances that build up in the water layer, due to the $\mathrm{Tan}(\beta l_{layer})$ factor. As the thin layer gets thinner than the depth at which the US pulse packet completely decays into water, the reflections becoming important. This rapid change in the reflectance coefficient can be used to track the thickness of the water layer as the reflected signal changes with thickness. Experimentally measured data on one pixel is shown in FIG. 3b where the y-axis is the return signal, and the x-axis is the time over which water is placed on the imaging area. This data was taken with the carrier frequency of the wave packets to be at 1.85 GHz. At the beginning of the experiment there is no water on the back side of the device, and the reflection signal corresponds to the reflection from silicon-air interface (FIG. 3*b* 301). The reflection coefficient is ~−1, leading to a zero pressure at the surface and results in highest return signal. As the water is added to the back side (302), the reflection coefficient drops reducing the return amplitude. There a few sharp changes owing to the water moving around on the active pixel area, that are artifacts of the water delivery process. The return signal eventually settles to the value corresponding to that of a thick water layer. As the water evaporates, the water layer thickness reduces, and starts approaching the thicknesses at which the reflection from the water-air interface starts adding constructively or destructively, thus resulting in resonant swings in the received signal (303). The multiple peaks and valleys correspond to the water thickness changing. Eventually the water completely evaporates, and the reflected wave amplitude increase to the level associated with the air reflection (304).

The resonances seen in the return signal as the layer thickness can be seen not only with the thickness of the layer changing, but also by the change in the acoustic impedance of the layer, and the ultrasonic frequency of the pulses. By sweeping the ultrasonic carrier frequency, the peak and valley of the resonances can be traversed. By measuring the change in the amplitude as a function of carrier frequency change in impedance can be tracked accurately with respect to thickness and the ultrasonic impedance of the sample. The response of the signal vs. frequency, an estimate of the thickness of the water layer down to fractions of the ultrasonic wavelength in the liquid layer. By having several pixels of the sense transducers working to image the surface, early detection of the spatial distribution of where the water is condensing can be captured. Hence, both the presence of the water and the thickness of the film can be measured.

Figure 4:
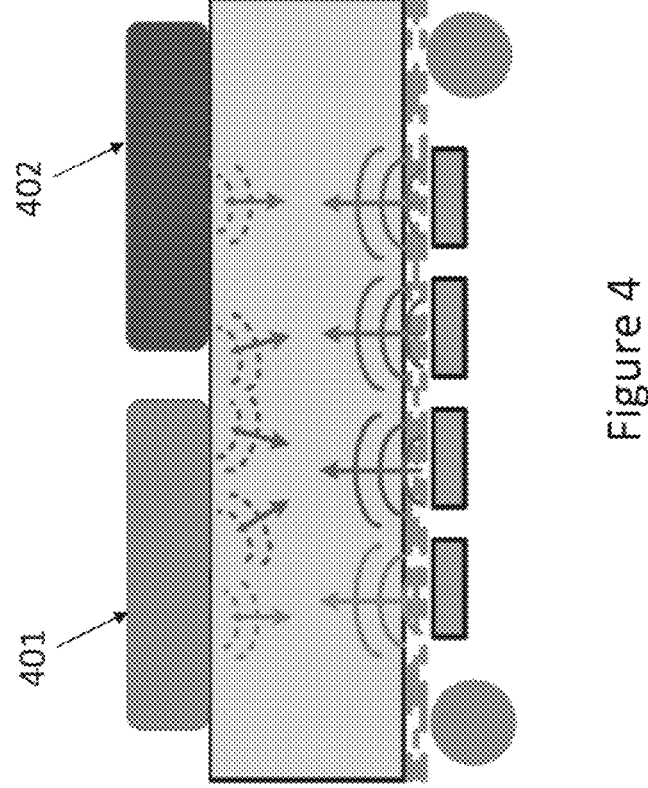
FIG. 4 is a schematic view of a sensor, in accordance with an embodiment.

In some applications, it is important to determine if a sample was exposed to air if packaged in dry gas such as nitrogen. A sensor can be formed by applying a thin layer of hygroscopic material 401 such as calcium carbonate on the US sensor (FIG. 4). As the moisture goes in and out of the film, the film's US impedance will change, allowing one to measure the thin film's exposure to moisture. The sensor chip can be placed inside bottles and interrogated using RF pulses through an integrated antenna or have the sensor interfaced to an RFID. The thin film of calcium carbonate can be formed by spin coating a solution, electrospray, thermal or e-beam evaporation, or by inject or pressure spray coating, potentially though a mask layer.

To sense exposure to oxygen, the thin layer can be a layer of material 402 that oxidizes when exposed to oxygen. One such material is iron. When iron reacts with oxygen, it will turn in iron-oxide. Since iron-oxide (Z=8.83 MRayls) and iron (Z=25.3 MRayls) have very different ultrasonic impedances, the return signal from the thin layer will change over time and be measured using the sensor (FIG. 4). An advantage of gigahertz frequency is that the wavelength can be small and the thin film structure can be thin, comparable to the wavelength. The film thickness to be used here can be very thin, for example in the order of 1-2 um, corresponding to the half-wavelength thickness of the sense material. For example, the speed of sound in iron is ~5920 m/s. At 1.85 GHz, the wavelength of ultrasonic waves is 3.2 micrometers. A half-wavelength resonator thickness would be 1.6 micrometers thick. This layer thickness is easy to achieve using thin film evaporation, electroplating techniques. As a way to measure oxidation differentially, the sensor can optionally include thin film islands made of materials that do not oxidize. These include materials such as gold or platinum. We can place thin film islands of different materials onto the imaging side using sequential deposition.

Figure 5:
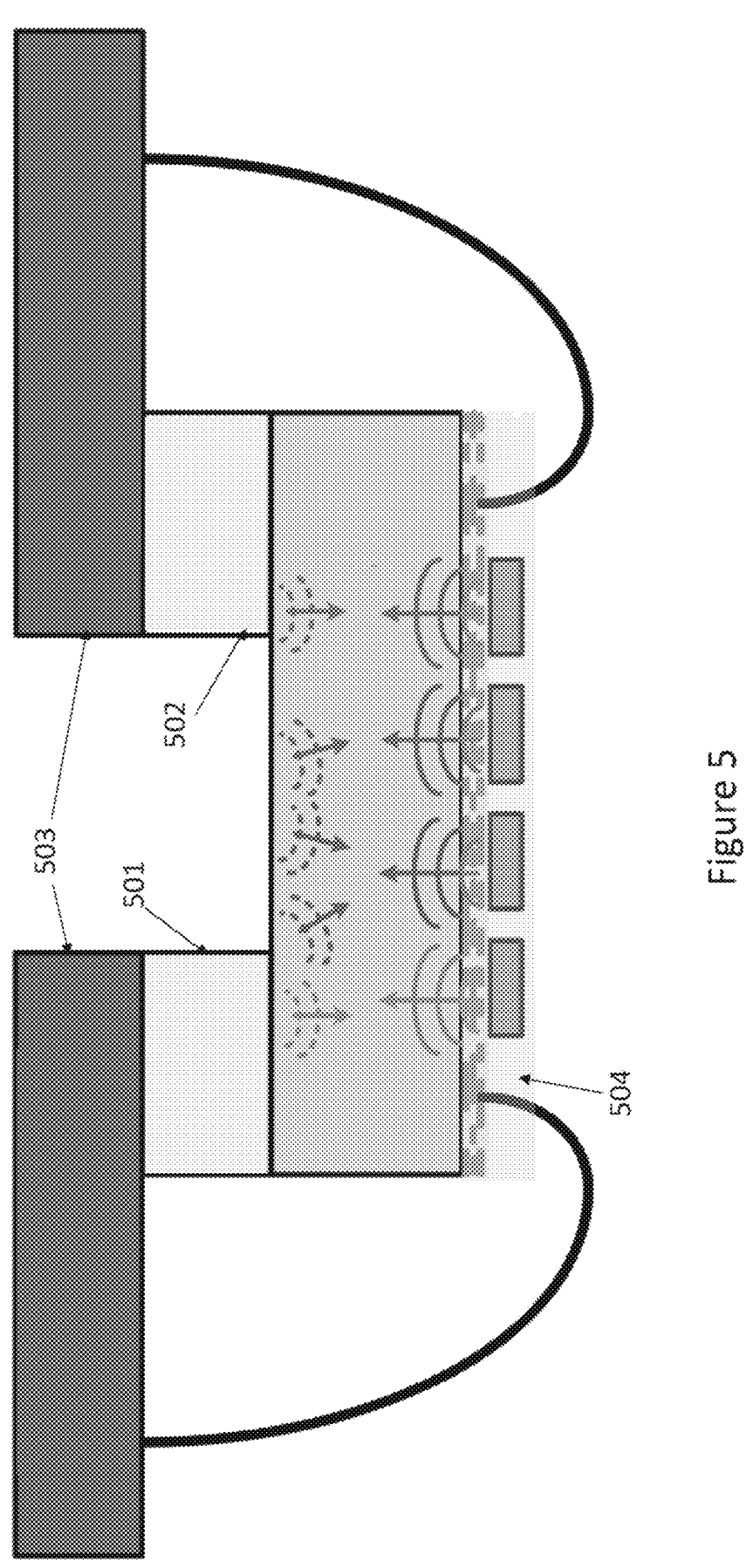
FIG. 5 is a schematic view of a sensor, in accordance with an embodiment.

Dew point is also a very important parameter to measure as described above. In addition to the measurement of moisture using the hygroscopic thin film above, the dew point can also be measured by cooling the ultrasonic imager chip to temperatures where the moisture will condense onto the imager surface. The cooling of the imager can be done with an active method to cool the silicon substrate. The cooling element can be a small Peltier cooling element 501 that can be attached to the chip and interfaced to the PCB 503 (FIG. 5). A second Peltier device or a polymer electrically and thermally insulating block 502 can be placed on the part of the periphery of the chip. A layer 504, consisting of a spin-coated or sprayed or applied polymer film can be applied to the CMOS side to prevent any water, due to condensation, to come in contact with the CMOS electronics. Furthermore, the film 504 thermally isolates the chip from the environment to result in a more uniform temperature in the silicon substrate. The Peltier device operates by moving heat from a cold side to a hot side by driving electrons and holes in alternating P and N type doped blocks. The Peltier device can remove the heat from the imager silicon chip and move it to a heat sink on the PCB, used here to show an example assembly method. Since the sensing/imaging CMOS chip can be very small with each ultrasonic pixel being only 50×50 um, the cooling thermal mass can be small, enabling very fast heating and cooling of the chip. As the substrate is cooled closer to the condensation temperature, any water in the environment will condense, and can be detected using the change in the ultrasonic reflectance. By closed loop control of the temperature, the sensor can maintain a minimum layer of water, to continuously determine the dew point in the environment.

Figure 6:
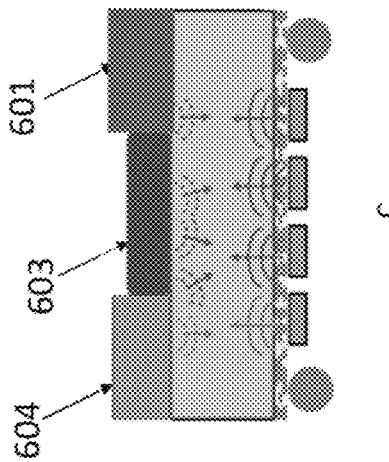
FIG. 6a is a schematic view of a sensor at the dry stage, in accordance with an embodiment.
FIG. 6b is a schematic view of a sensor at the wet stage, in accordance with an embodiment.
FIG. 6c is a schematic view of a sensor at the ice stage, in accordance with an embodiment.
Figure 6:
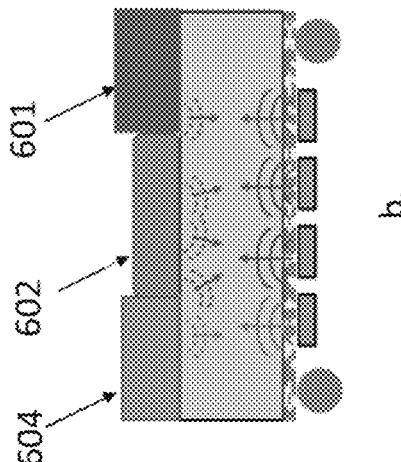
Figure 6:
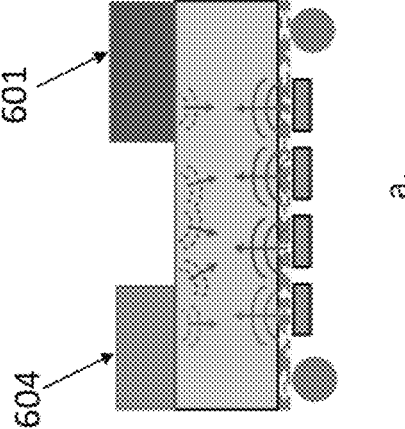

The ultrasonic pulses can also be used to measure the temperature. As the speed of sound changes in silicon with temperature, the return signal from substrate-layer interface changes in phase, owing to the modified path length for the ultrasonic pulse packet. To measure the temperature independently of the impedance effect of thin layer, an isolation layer will be placed on a subset of the pixels. This is shown as the polymer reflector 601 in FIGS. 6 and 502 in FIG. 5, as a simple block of epoxy can serve as material to isolate the pixels from any condensates. In addition to the measurement of the temperature using the ultrasonic transit phase in silicon, transistor and diode-based temperature sensors can also be used in the CMOS side to measure temperatures. Now as the temperature of the chip is reduced using the Peltier cooler, and the dew point is reached, the moisture in the air will condense on the surface forming a water layer 602. If the temperature is reduced further, the water can be frozen into a thin film of ice 603. Using the combination of measurement of the thin film thickness and temperature, the dew-point temperature and the freezing point of the liquids can be measured.

The pixels can be formed in a 2D array. The pixel array allows a user to see patterns of thin-film thickness changes. The entire imaging array can be coated with different combinations of thin film structures, varying in thickness and material, to extract different physical parameters. FIG. 2*a* shows a 2D array of 50×50 um pixels formed in a 128×128 array. The device's imaging capabilities can be used to determine the presence of contaminants on the surface and avoid using those pixels covered by contaminants. This attribute would enable the use of the sensor even when the surface has been contaminated with particles because there are more pixels available to sue that are not contaminated.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

What is claimed is:

1. A sensor, comprising:
a substrate having a first and a second side;
a piezoelectric ultrasonic transducer connected to the first side of the substrate and positioned to transmit a series of pulses into the substrate;
a layer of a material connected to the second side of the substrate, wherein the layer of the material is an evaporated metal layer that can chemically react with an environment; and
a set of circuits positioned on the first side of the substrate to receive any of the series of pulses that are reflected back through the substrate from the second side of the substrate and to detect any changes in ultrasonic impedance due to changes in the material of the layer of the material.

2. The sensor of claim 1, wherein the piezoelectric ultrasonic transducer operates at frequencies of at least 900 MHz.

3. The sensor of claim 1, wherein there are a plurality of piezoelectric ultrasonic transducers that are formed in an array.

4. The sensor of claim 1, wherein the substrate comprises integrated CMOS electronics.

5. The sensor of claim 1, further comprising a RF receiver and transmitter, including integrated antennas to enable remote measurement.

6. The sensor of claim 1, further comprising a 2D array of ultrasonic transducers for producing images of the layer of the material.

7. The sensor of claim 1, in which the thickness of the layer of the material is no greater than 5 micrometers.

8. The sensor of claim 1, further comprising a cooling element.

9. The sensor of claim 1, further comprising a heating element.

10. The sensor of claim 8, wherein a Peltier cooling element is connected to the sensor to cool and heat the substrate.

11. A sensor, comprising:
a substrate having a first and a second side;
a piezoelectric ultrasonic transducer connected to the first side of the substrate and positioned to transmit a series of pulses into the substrate;
a layer of a material connected to the second side of the substrate, wherein the layer of the material is an evaporated metal layer that can chemically react with an environment;
a set of circuits positioned on the first side of the substrate to receive any of the series of pulses that are reflected back through the substrate from the second side of the substrate and detect any changes in ultrasonic impedance due to changes in the the layer of the material; and
a cooling element connected to the second side of the substrate.

12. The sensor of claim 11, wherein the piezoelectric transducer operates at frequencies of at least 900 MHz.

13. The sensor of claim 11, wherein there are a plurality of piezoelectric transducers that are formed in an array.

14. The sensor of claim 11, wherein the substrate comprises integrated CMOS electronics.

15. The sensor of claim 11, further comprising a RF receiver and transmitter, including integrated antennas to enable remote measurement.

16. The sensor of claim 11, further comprising a 2D array of ultrasonic transducers for producing images of the layer of the material.

17. The sensor of claim 11, in which the thickness of the layer of the material is no greater than 5 micrometers.

* * * * *